(12) United States Patent
White et al.

(10) Patent No.: US 10,137,673 B2
(45) Date of Patent: Nov. 27, 2018

(54) METHODS AND SYSTEMS FOR CONTINUOUS FLOW CELL LYSIS IN A MICROFLUIDIC DEVICE

(71) Applicant: Canon U.S. Life Sciences, Inc., Rockville, MD (US)

(72) Inventors: Ian M. White, Ellicott City, MD (US); Jeffrey Burke, Silver Spring, MD (US); Kunal Pandit, Laurel, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 465 days.

(21) Appl. No.: 14/586,576

(22) Filed: Dec. 30, 2014

(65) Prior Publication Data

US 2015/0184127 A1    Jul. 2, 2015

Related U.S. Application Data

(60) Provisional application No. 61/971,084, filed on Mar. 27, 2014, provisional application No. 61/922,447, filed on Dec. 31, 2013.

(51) Int. Cl.
*B32B 37/00* (2006.01)
*C12N 1/06* (2006.01)
*C12M 1/00* (2006.01)
*B01L 3/00* (2006.01)

(52) U.S. Cl.
CPC .... *B32B 37/0076* (2013.01); *B01L 3/502707* (2013.01); *B01L 3/502761* (2013.01); *C12M 47/06* (2013.01); *C12N 1/066* (2013.01); *B01L 2200/0647* (2013.01); *B01L 2300/0816* (2013.01); *B01L 2400/086* (2013.01)

(58) Field of Classification Search
CPC .......... B32B 37/0076; B01L 3/502707; B01L 3/502761
See application file for complete search history.

(56) References Cited

U.S. PATENT DOCUMENTS

| | | |
|---|---|---|
| 4,992,312 A | 2/1991 | Frisch |
| 8,257,964 B2 | 9/2012 | Hung et al. |
| 2003/0178641 A1 * | 9/2003 | Blair ..................... B01F 5/0618 257/200 |

(Continued)

FOREIGN PATENT DOCUMENTS

WO    WO-2012170560 A2 *  12/2012    ............ C12M 47/10

OTHER PUBLICATIONS

Mun et al., "Continuous cell cross over and lysis in a microfluidic device," Microfluid Nanofluid, 8:695-701 (2010).

(Continued)

*Primary Examiner* — Daniel McNally
(74) *Attorney, Agent, or Firm* — Rothwell, Figg, Ernst & Manbeck, P.C.

(57) ABSTRACT

The present invention relates to methods and systems for cell lysis in a microfluidic device. More specifically, embodiments of the present invention relate to methods and systems for rapid continuous flow mechanical cell lysis. In one embodiment, a microfluidic device includes one or more microfluidic channels, each channel comprising constricted regions and non-constricted regions separating the constricted regions, wherein the constricted regions are configured to disrupt the cellular membranes of cells in fluid flowing through the one or more microfluidic channels.

24 Claims, 13 Drawing Sheets

(56) References Cited

U.S. PATENT DOCUMENTS

| | | | |
|---|---|---|---|
| 2004/0224397 | A1 | 11/2004 | Culbertson et al. |
| 2005/0053952 | A1* | 3/2005 | Hong .................. B01L 3/50273 435/6.14 |
| 2007/0031819 | A1 | 2/2007 | Koschwanez et al. |
| 2007/0178133 | A1* | 8/2007 | Rolland .................. A61L 27/18 424/423 |
| 2007/0275455 | A1* | 11/2007 | Hung ................. G01N 33/5008 435/287.1 |
| 2008/0070282 | A1* | 3/2008 | Hwang .................... B01L 7/52 435/91.2 |
| 2012/0149126 | A1* | 6/2012 | Wilson ............... B01D 11/0266 436/175 |
| 2012/0153526 | A1 | 6/2012 | Ko et al. |
| 2013/0228950 | A1 | 9/2013 | DeSimone et al. |
| 2013/0331528 | A1* | 12/2013 | Carlborg ............. C08G 77/392 525/477 |

OTHER PUBLICATIONS

Schilling et al., "Cell Lysis and Protein Extraction in a Microfluidic Device with Detection by a Fluorogenic Enzyme Assay," Anal. Chem. 74:1798-1804, (2002) abstract only.

Church et al., "Integrated electrical concentration and lysis of cells in a microfluidic chip," Biomicrofluidics 4:044101 (2010).

Wang et al., "A microfluidic flow-through device for high throughput electrical lysis of bacterial cells based on continuous dc voltage," Biosens. Bioelectron, 22(5):582-8 (2006) abstract only.

Belgrader et al., "A minisonicator to rapidly disrupt bacterial spores for DNA analysis," Anal. Chem., 71:4232-6 (1999) abstract only.

Taylor et al., "Lysing bacterial spores by sonication through a flexible interface in a microfluidic system," Anal. Chem., 73:492-6 (2001) abstract only.

Lee et al., "Microchip-based one step DNA extraction and real-time PCR in one chamber for rapid pathogen identification," Lab Chip, 6:886-95 (2006) abstract only.

Quinto-Su et al., "Examination of laser microbeam cell lysis in a PDMS microfluidic channel using time-resolved imaging," Lab Chip, 8:408-14 (2008) abstract only.

Di Carlo et al., "Reagentless mechanical cell lysis by nanoscale barbs in microchannels for sample preparation," Lab Chip, 3:287-291 (2003).

Wurm et al., "Mechanical disruption of mammalian cells in a microfluidic system and its numerical analysis based on computational fluid dynamics," Lab Chip, 12:1071-7 (2012) abstract only.

Duffy et al., "Rapid Prototyping of Microfluidic Systems in Poly(dimethylsiloxane)," Anal. Chem., 70:4974-4984 (Dec. 1, 1998).

Unger et al., "Monolithic Microfabricated Valves and Pumps by Multilayer Soft Lithography," Science, 288:113-6 (2000).

Sikanen et al., "Fabrication and bonding of thiol-ene-based microfluidic devices," J. Micromech. Microeng., 23:037002 (2013) abstract only.

\* cited by examiner

METHODS AND SYSTEMS FOR CONTINUOUS FLOW CELL LYSIS IN A MICROFLUIDIC DEVICE

CROSS-REFERENCE TO RELATED APPLICATIONS

This application claims the benefit of U.S. Provisional Patent Application Ser. No. 61/922,447, filed on Dec. 31, 2013, and U.S. Provisional Patent Application Ser. No. 61/971,084, filed on Mar. 27, 2014, which are incorporated herein by reference in their entirety.

BACKGROUND

Field of the Invention

The present invention relates to methods and systems for cell lysis. More specifically, embodiments of the present invention relate to methods and systems for rapid continuous flow cell lysis in a microfluidic device.

Discussion of the Background

Cell lysis has many different applications. To access the DNA from cells (including the enriched bacterial DNA in the circulating neutrophils of patients with bloodstream infections), it is necessary to lyse the cells. This can be challenging when a large number of cells need to be processed in a short amount of time (such as when lysing the neutrophils recovered from patients with bloodstream infections) in a microfluidic channel. For this case, the lysis must be "continuous-flow," which implies that traditional chemical lysis techniques cannot be used. In particular, the rapid processing of whole blood cells is useful for the diagnosis of bloodstream infections. While healthcare providers wait on current methods to process whole blood, it is necessary to use broad-range therapies to treat the infected patient, resulting in higher healthcare costs and increasing antibiotic resistance of pathogenic bacteria.

Although a number of techniques have reportedly been demonstrated for on-chip cell lysis, including chemical (Mun et al., Microfluid. Nonofluid. 8:695, 2009; Schilling et al., Anal. Chem. 74:1798, 2002), electrical (Church et al., Biomicrofluidics 4:044101, 2010; Wang et al., Biosens. Bioelectron. 22:582, 2006), acoustic (Belgrader et al., Anal. Chem. 71:4232, 1999; Taylor et al., Anal. Chem. 73:492, 2001), and optical (Lee et al., Lab Chip 6:886, 2006; Quinto-Su et al., Lab Chip 8:408, 2008) techniques, these methods require a high residence time in the microfluidic channel, and thus cannot be used for continuous-flow processing. Mechanical shearing of cells can offer the lysis speed to enable continuous-flow processing (e.g. 100 μL/min). The use of mechanical shearing for continuous-flow cell lysis has been reported in silicon devices using narrow channels with features on the scale of a few microns (see Di Carlo et al., Lab Chip 3:287, 2003; Wurm and Zeng, Lab Chip 12:1071, 2012). However, as the devices are silicon-based, they are not replica molded and thus are quite expensive and time-consuming to produce. Fabricating the devices with soft-lithography would dramatically improve the cost, but unfortunately soft materials are not compatible with the mechanical lysis concept due to significant channel expansion that such materials experience under the high fluid pressure required for continuous flow cell lysis.

The introduction of soft-lithography fabrication using the elastomer polydimethylsiloxane (PDMS) resulted in an expansion of research in the field of microfluidics (Duffy et al., Anal. Chem. 70:4974, 1998).

Two primary advantages of elastomer-based soft lithography drove this expansion of microfluidics research: (i) the low cost and ease of soft-lithography-based fabrication enabled rapid prototyping of devices, and (ii) the flexibility of the PDMS elastomer could be leveraged to fabricate actuated components, in particular valves and pumps (Unger et al., Science 288:113, 2000), into the microsystems. Thus, PDMS and soft lithography assisted in the evolution of microfluidic devices to a paradigm in which functional devices are fabricated through replica molding, which decreased the cost per device as compared to silicon- or glass-based devices.

While it is clear that soft lithography may be a valuable technique to the field of microfluidics, PDMS as a material for soft lithography has disadvantages in many important applications. For example, the vapor porosity of PDMS leads to evaporation of samples, the hydrophobicity of PDMS leads to challenges with wettability, and the deformability causes feature sizes to change under various pressure conditions. In particular, this lack of rigidity prohibits the use of PDMS for a number of applications that require fixed and predictable channel dimensions under high pressure.

One such application for which PDMS is inappropriate is rapid and continuous-flow cell lysis in a microfluidic channel.

Other polymers used as materials for soft lithography is off-stoichiometry thiol-ene (OSTE) polymer. OSTE polymers have been directly bonded using the reactive groups present on the surface, such as the bonding of two OSTE prepolymers, one OSTE prepolymer with an excess of thiol groups and the other OSTE prepolymer with an excess of allyl (or -ene) groups. The two prepolymers will react to covalently link themselves under UV exposure. One disadvantage of this method is that it requires two OSTE prepolymer formulations for bonding. The bonding of an OSTE prepolymer to itself has been reported (see Sikanen et al., J. Micromech. Microeng. 23:037002, 2013). In this case, two pieces of fully cured OSTE polymer made from an OSTE prepolymer with excess allyl groups were contacted and exposed to UV. Although bonding can be achieved with this method, contacting fully cured OSTE polymer pieces results in a bond strength that varies across assembled devices. In principle, full curing of the OSTE polymer will consume all (or most) of the thiol groups, leaving allyl groups at the surface. The allyl groups cannot react with each other to form covalent bonds. For the two fully cured pieces to bond, unreacted thiol groups must be present at the surface. The small number of unreacted thiol groups present after fully curing is not sufficient to achieve consistent bonding.

Although various methods exist to lyse cells, none of these methods describes a single device that is capable of rapid continuous flow cell lysis. Thus, there is a need to develop microfluidic systems and methods for rapid continuous flow cell lysis.

SUMMARY

The present invention relates to methods and systems for rapid continuous flow cell lysis. More specifically, embodiments of the present invention relate to methods and systems for the isolation of cells on a microfluidic device by means of mechanical shearing. Embodiments of the present invention also relate to the fabrication of these devices.

In one aspect, the present invention provides a method for fabricating a microfluidic device using soft-lithography replica molding. In one embodiment, the method comprises fabricating a first piece of the microfluidic device in a mold.

In some embodiments, fabricating the first piece comprises pouring a first layer of thermoplastic prepolymer onto the mold. Fabricating the first piece further comprises partially curing the first layer under exposure to UV-light. In some embodiments, the method further comprises fabricating a second piece of the microfluidic device on a glass slide by coating the glass slide with a layer of the thermoplastic prepolymer. In some embodiments, fabricating the second piece further comprises partially curing the layer coated on the glass slide under exposure to UV-light. In some embodiments, the method further comprises removing the first piece from the mold and contacting the first piece to the second piece. In some embodiments, the method further comprises bonding the first piece and the second piece together on the glass slide by curing the contacted first and second pieces under exposure to UV-light.

In some embodiments, bonding the first piece and the second piece together on the glass slide further comprises baking the first and second pieces. In additional embodiments, fabricating the first piece further comprises pouring a second layer of the thermoplastic prepolymer onto the mold. In some embodiments, fabricating the first piece further comprises degassing the second layer under vacuum. In some embodiments, fabricating the first piece further comprises removing any air bubbles from the first piece.

In some embodiments, the thermoplastic polymer comprises an off-stoichiometry thiol-ene (OSTE) polymer made from an OSTE prepolymer having an excess of allyl groups. In some embodiments, bonding the first piece and the second piece together on the glass slide further comprises baking the first and second pieces at a temperature close to the glass transition temperature of the OSTE polymer.

In some embodiments, fabricating the first piece of the microfluidic device further comprises applying a release agent onto the mold. In additional embodiments, fabricating the first piece of the microfluidic device further comprises degassing the first layer under vacuum. In some embodiments, fabricating the second piece of the microfluidic device further comprises applying a release agent onto the glass.

In some embodiments, a microfluidic device is fabricated to include one or more channels having one or more constrictions configured to lyse cells.

In one aspect, the present invention provides a microfluidic device for lysing cells. In one embodiment, the microfluidic device comprises one or more microfluidic channels, each channel comprising constricted regions and non-constricted regions separating the constricted regions, wherein the constricted regions are configured to disrupt the cellular membranes of cells present in fluid flowing through the one or more microfluidic channels.

In some embodiments, the non-constricted regions are arranged in a honeycomb-like pattern. In some embodiments, the microfluidic channels are parallel to each other. In additional embodiments, the width of the non-constricted regions is 40-100 µm and the width of the constricted regions is 3-10 µm. In some embodiments, the length of the non-constricted regions is 60-120 µm and the length of the constricted regions is 10-20 µm.

In some embodiments there are 1-40 microfluidic channels. In some embodiments, each microfluidic channel has 3-15 constricted regions. In some embodiments, each constricted region has a width of 3-10 µm. In some embodiments, a first segment of the constricted regions along a fluid flow path have a width of 6-8 µm and a second segment of the constricted regions along a fluid flow path have a width of 4-6 µm. In other embodiments, each microfluidic channel has 10 constricted regions. In some embodiments, there are 1, 10, 20, or 40 microfluidic channels. In some embodiments, each microfluidic channel has 10 constricted regions, wherein the first five constricted regions along a fluid flow path have a width of 6.5 µm and the last five constricted regions along the fluid flow path have a width of 5 µm. In some embodiments, the width of the constricted regions is 2.5-4.5 µm. In some embodiments each of the microfluidic channels has 4 constricted regions and each constricted region has a width of 3 µm.

In some embodiments, the microfluidic channels are configured to support a flow rate sufficient to cause increased (mechanical) shear stress on the cells passing through the constructed regions as described herein. In some embodiments, the flow rate may be from about 20 to about 2000 µL/min. In other embodiments, the flow rate may be from about 20 to about 1000 µL/min. In still other embodiments, the flow rate may be from about 50 to about 500 µL/min. In further embodiments, the flow rate may be from about 50 to about 200 µL/min. In additional embodiments, the microfluidic device is configured to support a cell-lysis rate of 85-100%.

In some embodiments, the microfluidic device is made of a thermoplastic polymer. In additional embodiments, the microfluidic device is configured to withstand high fluid pressure without deformation of the constricted regions.

In another aspect, the present invention provides a method for continuous flow cell lysis in a microfluidic device. In one embodiment, the method comprises causing fluid containing cells to flow through the microfluidic device, whereby cells in the fluid are lysed. In some embodiments, the microfluidic device comprises one or more microfluidic channels and each channel comprises constricted regions and non-constricted regions separating the constricted regions. In some embodiments, the constricted regions are configured to disrupt the cellular membranes of cells in fluid flowing through the one or more microfluidic channels as described herein.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF PREFERRED EMBODIMENTS

According to an embodiment of the present invention, a soft-lithography-based fabrication of rigid microsystems for the application of rapid and continuous-flow cell lysis is disclosed. In one non-limiting embodiment, this is accomplished through the use of a thermoplastic polymer prepared from a thermoplastic prepolymer in combination with a novel bonding procedure. In some embodiments, the thermoplastic polymer may comprise an off-stoichiometry thiol-ene (OSTE) polymer. In other embodiments, the OSTE polymer is made from a prepolymer having an excess of allyl functionality. In one embodiment, such a prepolymer is, for example, the OSTEmer Allyl 30 prepolymer from Mercene Labs, Stockholm, Sweden.

This OSTE polymer, as with PDMS, can be replica molded using soft-lithography techniques, but unlike PDMS, is rigid when fully cured. By utilizing a large stoichiometric excess of the reactive monomers, the surface and mechanical properties of the OSTE substrates can be tuned. In one non-limiting embodiment, a formulation with 30% excess ene (allyl) functionality yields a rigid polymer when cured. This formulation has a reported Young's modulus of 1740 MPa compared to 0.8 MPa for PDMS (see Carlborg et al., Lab Chip 11:3136, 2011). [PLEASE CONFIRM THAT THIS IS ACCURATE]

Figure 1:
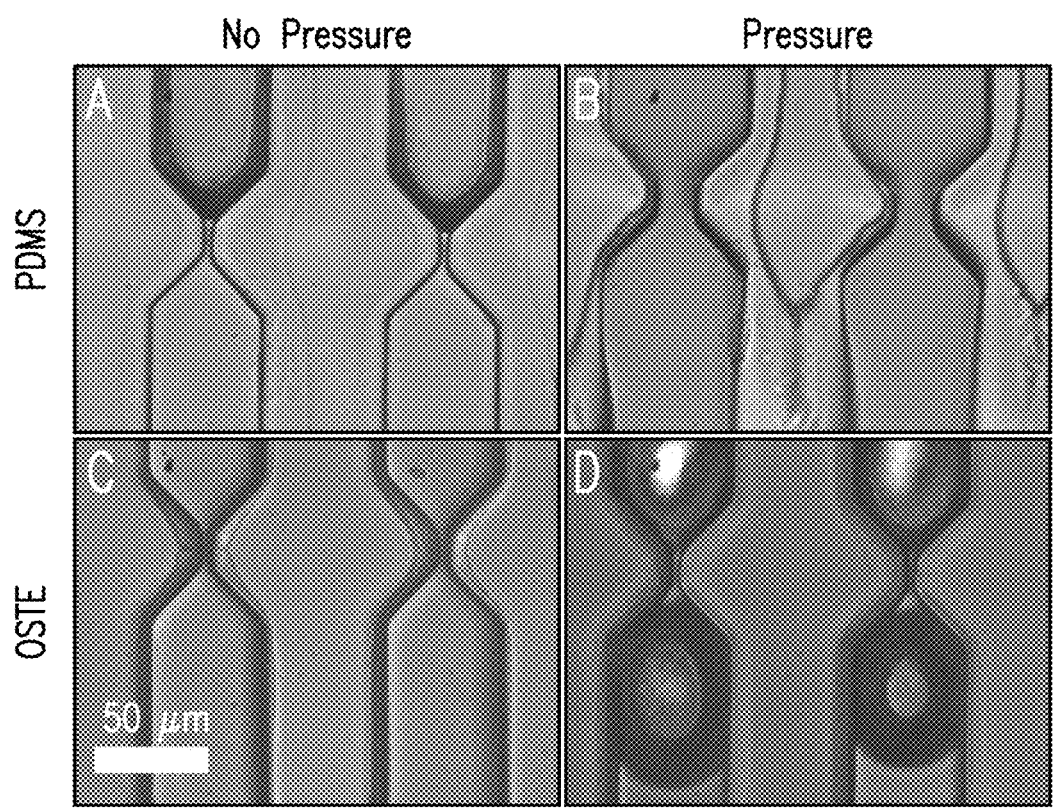
FIG. 1 shows a photograph comparing microfluidic channels made of PDMS- and OSTE-based polymers both under pressure and without pressure.

One disadvantage of PDMS for use in cell lysis is its lack of rigidity when fully cured. FIG. 1 shows a photograph comparing microfluidic channels made of a PDMS polymer and an OSTE polymer made in accordance with an embodiment of the present invention under pressure and without pressure. As illustrated in FIG. 1, when fluid flows under high pressure (for example, at 100 µL/min) through the channels made of PDMS, the constricted regions expand significantly (for example, to ~20 µm as illustrated). The expansion of the constricted regions makes PDMS less useful as a material for rapid continuous flow cell lysis, particularly for cells, such as MDA-MB-231, which are able to change shape, for example, by becoming elongated. As a result, the cells pass through the (expanded) PDMS constriction without experiencing high shear (or high energy dissipation rate (EDR)). In contrast, the channels made of OSTE polymer in accordance with an embodiment of the invention are rigid and maintain their features. Such channels are thus useful for cells including those that can change shape In one embodiment of the invention, a simple bonding technique is introduced for devices fabricated of a thermoplastic polymer (such as an OSTE polymer) that is much simpler than bonding methods for typical rigid materials (such as some thermal plastics and silica). In this embodiment, a thermoplastic prepolymer is only partially cured on the mold; i.e., the partially cured polymer (such as a partially cured OSTE polymer) can be removed from the mold without loss of features, but still remain soft. The device is then assembled and fully cured, as explained in greater detail below.

In one embodiment of the present invention, the bonding technique utilizes a modified allyl to allyl method. In this embodiment, an OSTE prepolymer having an excess of allyl groups is only partially cured on the mold; i.e., the partially cured OSTE polymer can be removed from the mold without loss of features, though it is not completely rigid. This results in a larger number of unreacted thiol groups at the surface. The OSTE polymeric device is then assembled and fully cured by UV exposure. The final cure consistently bonds the two OSTE polymeric pieces together.

Figure 2:
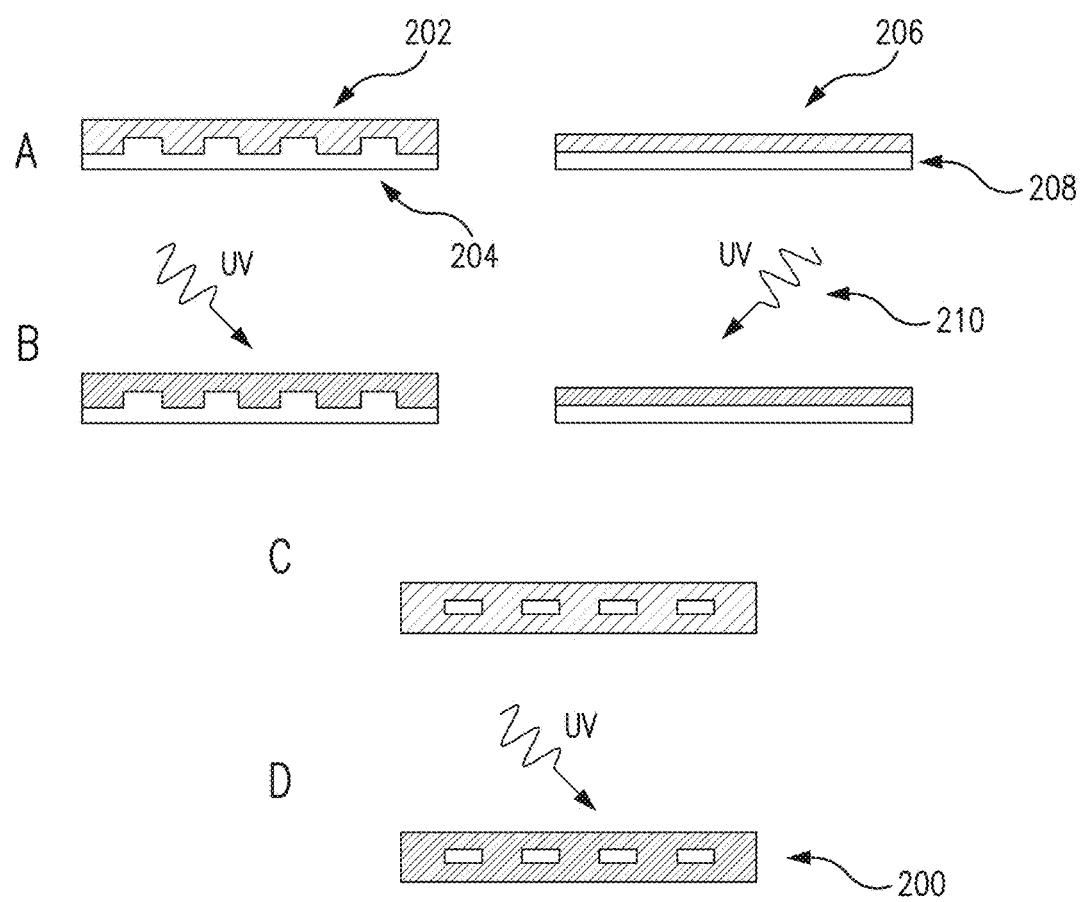
FIG. 2 is a flow chart illustrating a soft-lithography chip fabrication process for fabricating a microfluidic device according to an embodiment of the invention.

FIG. 2 shows a schematic illustration of the soft-lithography chip-fabrication process in accordance with an embodiment of the present invention. In one embodiment, as illustrated in FIG. 2, a first piece 202 of the microfluidic device 200 is fabricated in a mold 204. In some embodiments, the first piece 202 comprises a thermoplastic polymer. In some embodiments, a second piece 206 of the microfluidic device is fabricated on a glass slide 208. In some embodiments, the second piece 206 comprises the thermoplastic polymer. In some embodiments, the first piece 202 is removed from the mold 204 and placed in contact with the second piece 206. In some embodiments, the contacted first 202 and second 206 pieces of the microfluidic device are bonded together by fully curing them under exposure to UV radiation 210, resulting in a microfluidic device 200.

Figure 3:
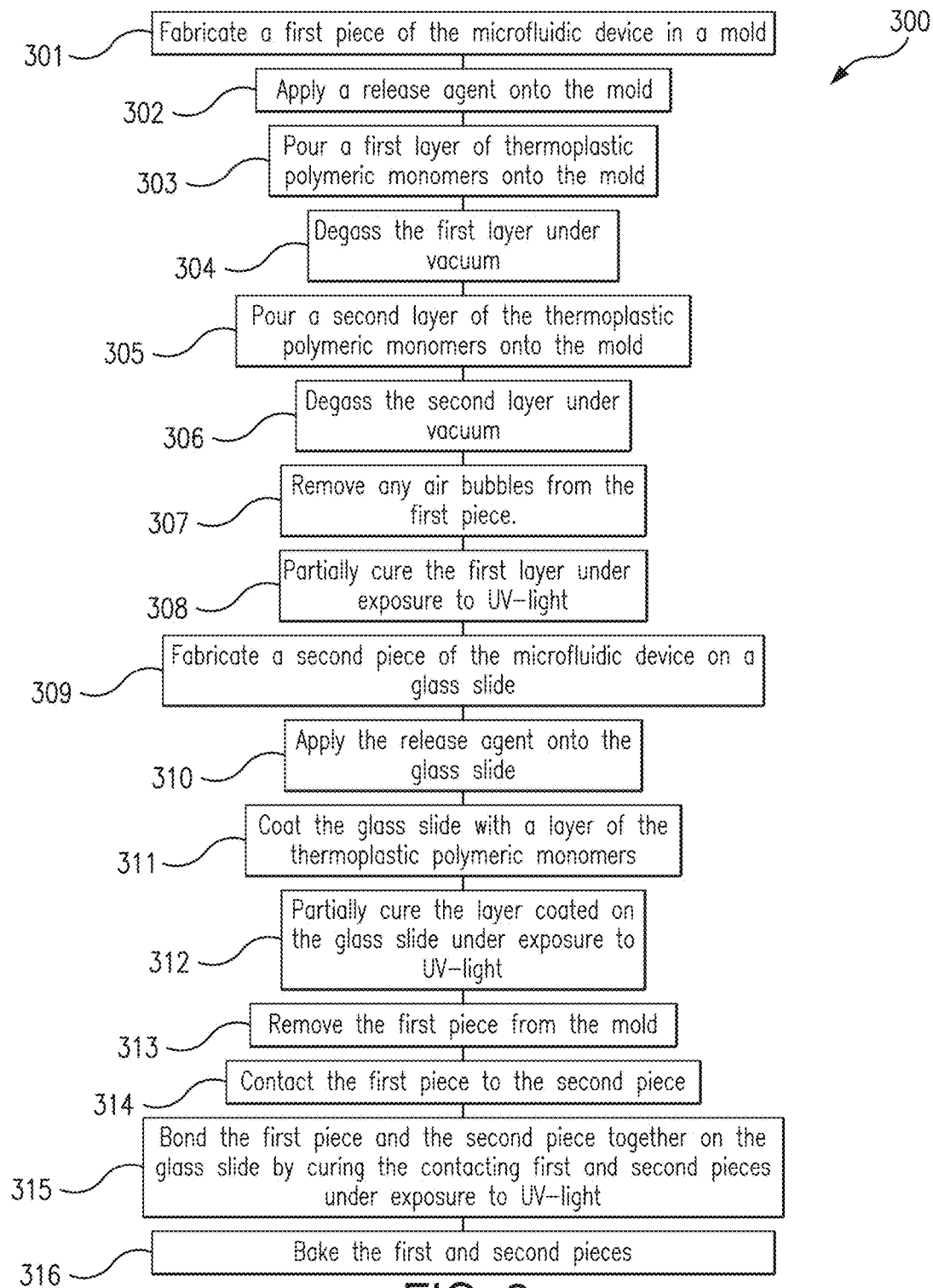
FIG. 3 shows a schematic illustration of the soft-lithography chip-fabrication process according to an embodiment of the invention.

A process for fabricating a microfluidic device according to an embodiment of the invention is described in greater detail in connection with the flow chart illustrated in FIG. 3. In one embodiment, process 300 may begin by fabricating a first piece of the microfluidic device on a mold (step 301). A second piece of the microfluidic device is fabricated on a glass slide (step 309). The first (step 308) and second (step 312) pieces of the microfluidic device are partially cured with UV radiation. The first piece of the microfluidic device is removed from the mold (step 313) and placed in contact with the second piece of the microfluidic device on the glass slide (step 314). Then, the first and second pieces of the microfluidic device are bonded together by fully curing the pieces under UV radiation (step 315), resulting in a microfluidic device.

In some embodiments, fabricating the first piece of the microfluidic device on a mold (step 301) comprises pouring a first layer of a thermoplastic prepolymer (such as, for example, an OSTEmer Allyl 30 prepolymer) onto the mold (step 303). In some embodiments, the first layer is then optionally degassed under vacuum (step 306). Fabricating the first piece of the microfluidic device further comprises partially curing the first layer under exposure to UV-light (step 308). In some embodiments, fabricating the second piece of the microfluidic device on a glass slide (step 309) comprises coating the glass slide with a layer of the thermoplastic prepolymer (step 311) and partially curing the layer under exposure to UV-light (step 312).

In a preferred embodiment, the mold (such as, for example, mold 204) is a silicon mold. The UV-radiation (such as, for example, UV-radiation 210) is preferably 365 nm UV-light, such as, for example, from a 100 W UV lamp. The first and second pieces of the microfluidic device (such as, for example, pieces 202 and 206) are preferably made from an OSTE prepolymer, such as, for example, an OSTEmer Allyl 30 prepolymer.

In a non-limiting example, the first piece of the microfluidic device may be fabricated by pouring a thin layer of an OSTEmer Allyl 30 prepolymer over a silicon master mold (step 303) and degassing the layer under vacuum for 10 minutes (step 304). The first piece of the microfluidic device may then be exposed to, for example, 365 nm UV-light at a distance of, for example, 6 inches for 35 seconds using a 100 W UV-lamp (step 308). The second piece of the microfluidic device may be fabricated by coating a glass slide with a thin layer of the OSTEmer Allyl 30 prepolymer (e.g. 1 mm) (step 311) and cured (step 312), for example, using UV-light for 40 seconds. The first piece of the microfluidic device may be removed from the mold (for example, by peeling it off the mold) (step 313), and contacted with the second piece of the microfluidic device on the glass slide (step 314). The contacted pieces of the microfluidic device may then be exposed to UV-light for, for example, 5 minutes (step 315). This exposure allows for complete bonding of the molded channels to the polymer-coated glass slide.

In some embodiments, fabricating the first piece of the microfluidic device on the mold (step 301) may begin by applying a release agent onto the mold (step 302). Fabricating the first piece of the microfluidic device further comprises pouring a first layer of thermoplastic prepolymer onto the mold (step 303). In some embodiments, fabricating the first piece of the microfluidic device may further comprise degassing the first layer under vacuum (step 304). In some embodiments, fabricating the first piece of the microfluidic device may further comprise pouring a second layer of the thermoplastic prepolymer onto the mold (step 305) and degassing the second layer under vacuum (step 306). In some embodiments, any air bubbles remaining in the first piece of the microfluidic device after degassing are removed, for example, by tilting the mold (step 307). Fabricating the first piece of the microfluidic device further comprises partially curing the first layer (and optional second layer) under exposure to UV-light (step 308). In some embodiments, fabricating the second piece of the microfluidic device may begin by applying a release agent onto the glass slide (step 310). Fabricating the second piece of the microfluidic device further comprises coating the glass slide with a layer of the thermoplastic prepolymer (step 311) and partially curing the coated layer under exposure to UV-light (step 312). In some embodiments, bonding the first and second pieces of the microfluidic device together on the glass slide by curing the contacted first and second pieces of the microfluidic device under exposure to UV-light (step 315) further comprises baking the pieces of the microfluidic device to finish the curing process (step 316).

As a non-limiting example, the thermoplastic prepolymer (for example an OSTE prepolymer, such as an OSTEmer Ally 30 prepolymer) may be brought to room temperature prior to fabrication. Fabricating the first piece of the microfluidic device may begin by applying a release agent onto a silicon mold, for example, by spraying a light mist of Ease Release 200 twice and allowing the mold to stand for 5 minutes. Fabricating the first piece of the microfluidic device may further comprise pouring a first layer of an OSTEmer Allyl 30 prepolymer onto the mold. The first layer may be approximately 0.5 mm. In one embodiment, fabricating the first piece of the microfluidic device may further comprise degassing the first layer under vacuum for 5 minutes before pouring a second layer of the OSTEmer Allyl 30 prepolymer onto the mold. The second layer may comprise approximately 0.5 mm. In one embodiment, fabricating the first piece of the microfluidic device may further comprise degassing the first and second layers under vacuum for 20 minutes and then removing any remaining air bubbles by tilting the mold. In one embodiment, fabricating the first piece of the microfluidic device may further comprise partially curing the first and second layers under a 100 W handheld UV-lamp at a distance of 13 cm for 50 seconds.

Also in accordance with a non-limiting example, fabricating the second piece of the microfluidic device may begin by applying a release agent onto the glass slide, for example, by spraying a light mist of Ease Release 200 twice and allowing the glass slide to stand for 5 minutes. Fabricating the second piece of the microfluidic device may further comprise coating the glass slide with a layer of the OSTEmer Allyl 30 prepolymer and partially curing the coated layer under exposure to UV-light for 30 seconds.

Also in accordance with a non-limiting example, removing the first piece of the microfluidic device from the mold may further comprise trimming the first piece of the microfluidic device, for example, with scissors and may further comprise baking the first piece of the microfluidic device for 1 minute at a temperature close to the glass transition temperature (e.g. 68° C. for OSTEmer Allyl 30 thermoplastic polymer) and then forming access holes in the first piece of the microfluidic device using a 1.2 mm biopsy punch. Bonding the first piece and the second piece of the microfluidic device together may comprise, for example, curing the pieces in contact with each other for 2 minutes under UV-exposure and baking the pieces for 10 minutes to finish the curing process. Before finishing the curing process, tubing may be inserted into the microfluidic device and held in place with the OSTE polymer made from an OSTEmer Allyl 30 prepolymer cured around it.

Figure 4:
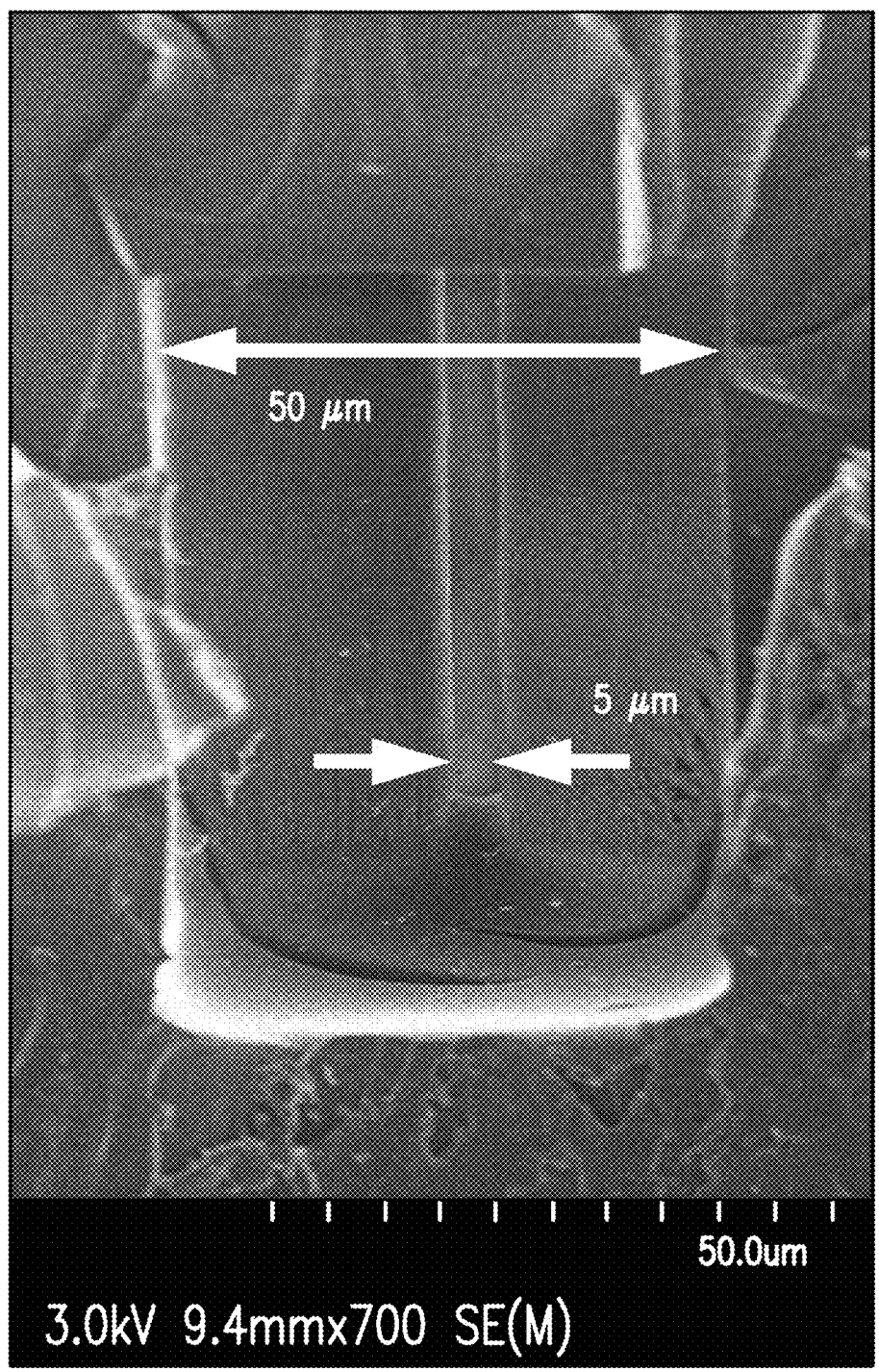
FIG. 4 shows a photograph of a chip cross section in accordance with an embodiment of the invention.

FIG. 4 shows a photograph of a cross section of a channel on a chip made in accordance with an embodiment of the invention. In particular, FIG. 4 illustrates a Scanning Electron Microscope (SEM) image of a microfluidic device with an OSTEmer Allyl 30 prepolymer used to make the thermoplastic polymer. Because the material is partially cured prior to bonding, one possible concern would be distortion or closing of the narrow constrictions of the constricted regions, especially due to the high aspect ratio (depth to width) of 15 in the non-limiting embodiment shown in FIG. 4. However, as shown in FIG. 4, the microfluidic channels remain open with straight sidewalls. The widths of the channels match those of the silicon master mold, such as silicon master mold 204. In addition, the microfluidic device is well bonded with almost no noticeable indication of the bonding surface.

Figure 5:
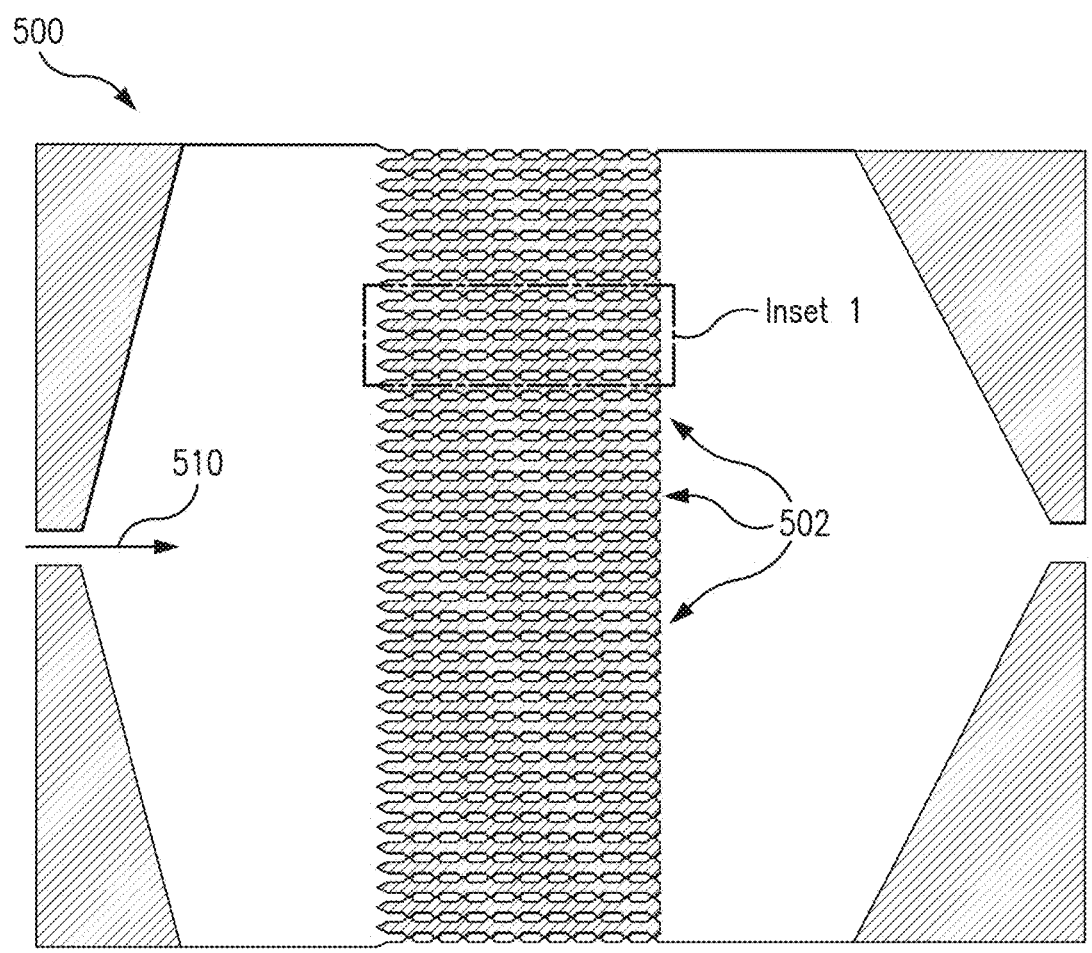
FIG. 5 shows a schematic illustration of a photomask for a microfluidic device in accordance with an embodiment of the invention.
Figure 6:
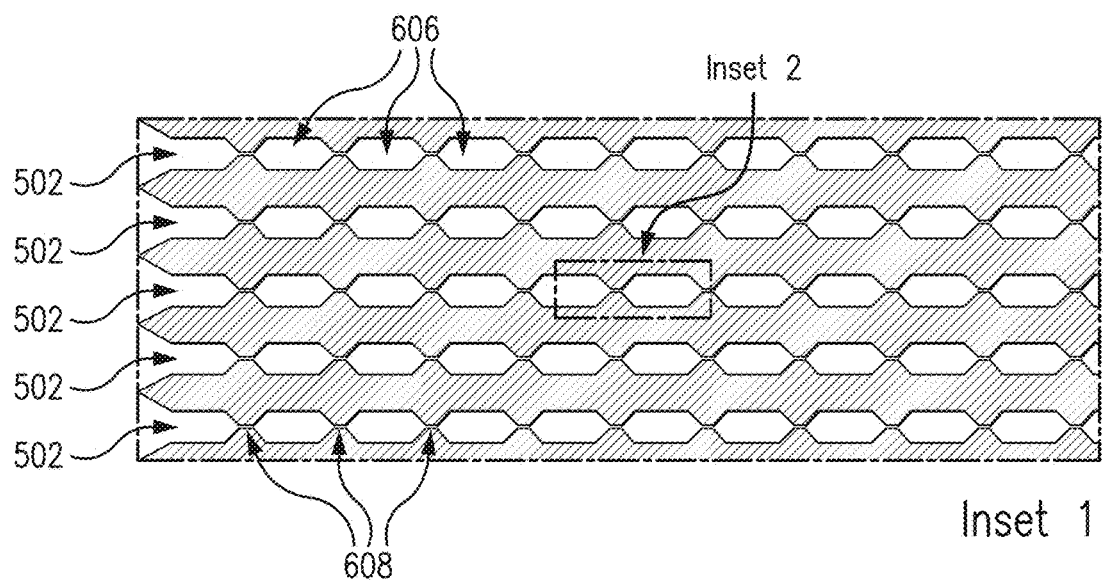
FIG. 6 shows a close-up view of a region of FIG. 5.
Figure 7:
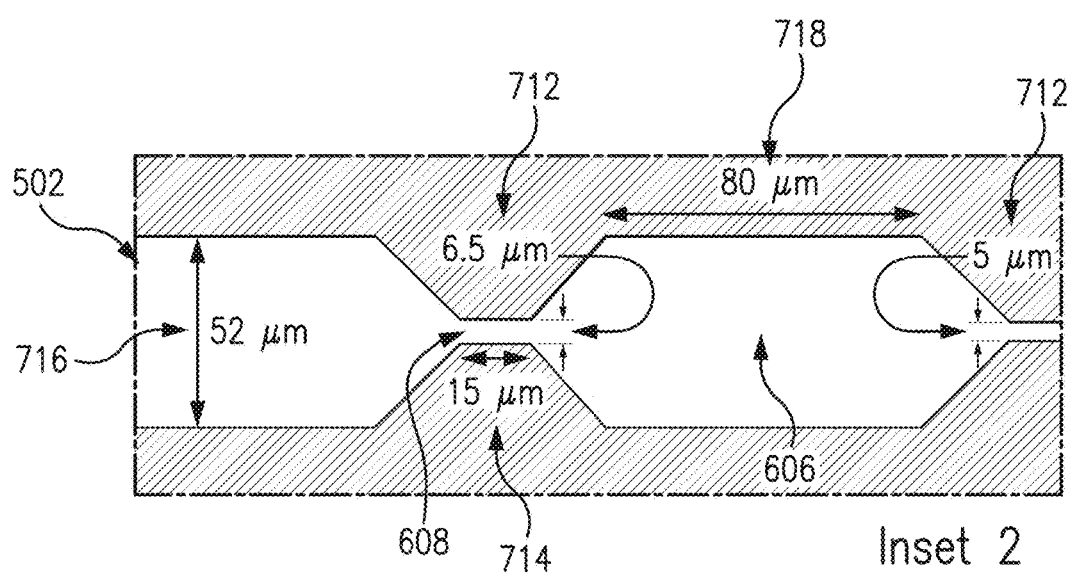
FIG. 7 shows a close-up view of a region of FIG. 6.

In an embodiment of the invention, in order to fabricate the mold (e.g. mold 204) used in the fabrication of the microfluidic device, a photomask may be used. FIGS. 5-7 show a schematic illustration of a photomask 500 for a microfluidic device in accordance with a non-limiting embodiment of the invention. As is known in the art, the photomask 500 can be used to create a mold (e.g. mold 204). For example, the photomask 500 can be used to etch a silicon wafer using deep reactive ion etching (DRIE), resulting in a silicon mold (e.g. mold 204).

As a non-limiting example, a master mold (e.g. mold 204) may be formed by spin coating photoresist (for example, Shipley 1813) onto a silicon wafer to a thickness of 3 μm, pre-baking the silicon wafer for 1 min at 95° C., and exposing the silicon wafer to 365 nm UV for 13 seconds. The photoresist may be developed, for example, for 75 seconds in Microposit developer CD-30 (Shipley). The silicon wafer may then be etched at a rate of, for example, ~2 μm/min to a depth of 70 μm with deep reactive ion etching (DRIE) using the photoresist as the mask 500. The resist may be stripped, for example, by using Remover PG (MicroChemCorp.).

In one embodiment, this fabrication process enables the fabrication of microfluidic devices having microfluidic channels 502 that can support high fluid flow rates (e.g. more than 100 μL/min) without features of the microfluidic channels 502 deforming under the resulting pressure (see, for example, FIG. 1). One application of such devices is rapid and continuous flow cell lysis in a microfluidic channel 502.

In one embodiment of the invention, FIGS. 5-7 illustrate microfluidic channels 502 on the photomask 500. The photomask 500 may, in some embodiments, be used to create a mold (e.g. mold 204). The mold may be used, in some embodiments, to create a microfluidic device, such as, for example, the microfluidic device 800 shown in FIG. 8.

In one embodiment, the microfluidic device 800 may comprise one or more microfluidic channels 502. In some non-limiting embodiments, the microfluidic device 800 may comprise 1-40 microfluidic channels 502. Each microfluidic channel 502 comprises constricted regions 608 and non-constricted regions 606 separating the constricted regions 608, wherein the constricted regions 608 are configured to disrupt the cellular membranes of cells in fluid flowing through the microfluidic channel 502 in a fluid flow direction 510. In some embodiments, the microfluidic channels 502 may comprise 4-20 constricted regions 608, or possibly more. In some embodiments, each microfluidic channel 502 comprises the same number of constricted regions 608, while in other embodiments, the microfluidic channels 502 may comprise differing numbers of constricted regions 608.

Figure 8:
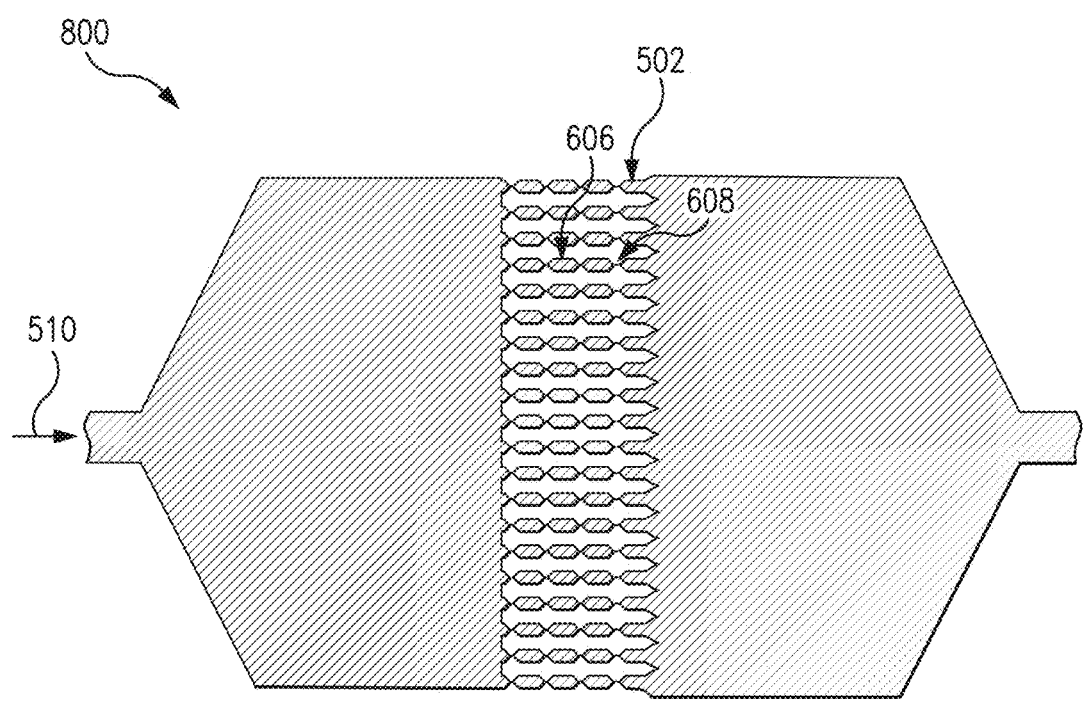
FIG. 8 shows a schematic illustration of a microfluidic device in accordance with an embodiment of the invention.

The microfluidic channels 502 are also shown in FIGS. 5, 6, and 8 to be parallel to each other. As will be appreciated, this is not a requirement and other arrangements are possible.

In an embodiment, the constricted regions 608 comprise a constricted width 712 and a constricted length 714. The non-constricted regions 606 comprise a non-constricted width 716 and a non-constricted length 718. In some embodiments, the constricted width 712 may be 3-10 μm and the constricted length 714 may be 10-20 μm. In some embodiments, the non-constricted width 716 may be 40-100 μm and the non-constricted length 718 may be 60-120 μm. In some embodiments, the constricted widths 712 and lengths 714 of the constricted regions 608 within a single microfluidic channel 502 may be the same constricted widths and lengths, while in other embodiments the constricted widths and lengths may differ. In some embodiments, the non-constricted widths 716 and lengths 718 of the non-constricted regions 606 within a single microfluidic channel 502 may be the same non-constricted widths 716 and lengths 718, while in other embodiments the non-constricted widths 716 and lengths 718 may differ. In some embodiments, the widths and lengths of the constricted 608 and non-constricted 606 regions for one microfluidic channel 502 may be the same as for another microfluidic channel 502, while in other embodiments different microfluidic channels 502 within the microfluidic device may comprise differing widths and lengths of the constricted 608 and non-constricted 606 regions.

In some embodiments, for example, the number and dimensions of the constricted 608 and non-constricted 606 regions may differ both within and between microfluidic channels 502, to achieve more diverse cell-lysing properties.

As a non-limiting example, a fluid being flowed through the microfluidic device 800 may comprise multiple types of cells each having different cell properties (e.g. size, flexibility, strength of cell membrane or wall), and differing arrangements of constricted 608 and non-constricted 606 regions may be preferred to effectively lyse the different types and sizes of cells. In some embodiments, cells of specific types may be directed to flow through specific microfluidic channels 502 designed to lyse that type of cell.

In one non-limiting example, a microfluidic device 800 may comprise 18 microfluidic channels 502 each having 1 constricted region 608 with a 3 μm constricted width 712.

In another non-limiting example, a microfluidic device 800 may comprise 20 microfluidic channels 502 each having 4 constricted regions 608 with a 3 μm constricted width 712.

In another non-limiting example, a microfluidic device 800 may comprise 20 microfluidic channels 502 each having 4 constricted regions 608 with a 5 μm constricted width 712.

In another non-limiting example, a microfluidic device 800 may comprise 40 microfluidic channels 502 each having 10 constricted regions 608. The constricted width 712 may be 6.5 μm in the first five constricted regions 608 along the fluid flow path 510, and 5.5 μm in the last five constricted regions 608 along the fluid flow path 510. The constricted length 714 may be 15 μm. The non-constricted width 716 may be 52 μm and the non-constricted length 718 may be 80 μm.

As will be appreciated, the design and number of microfluidic channels 502 and the number and dimensions (for example width and length) of the constricted regions 608 and non-constricted regions 606 may be chosen to accommodate different fluid flow rates (for example, 100 μL/min), and to have different back pressure and clogging characteristics. As will also be appreciated, the type of cells to be lysed (e.g. mammalian cells such as red blood cells, bacterial cells, fungal cells, metastatic cancer cells) will also affect the choice of design, number, and dimension of the microfluidic channels 502 and the constricted 608 and non-constricted 606 regions. For example, the size, flexibility, and strength of the cellular membrane or wall of the cells to be lysed may be important considerations in designing a microfluidic device 800.

As illustrated in FIGS. 5-7, the non-constricted regions 606 can, in one embodiment, be hexagonally shaped, converging at the ends into the constricted regions 608. This hexagonal or honeycomb-like arrangement of the non-constricted regions 606 provides for an efficient use of materials and helps to control the fluid flow in the microfluidic channels 502. As will be appreciated, other shapes and arrangements are possible, such as, for example, oval, trapezoidal, and serpentine arrangements. In some embodiments, where a constricted region 608 is in fluid communication with a non-constricted region 606, the channel walls protrude at an angle, eventually forming a hexagonal shape for the non-constricted region 606. As will be appreciated, other arrangements are possible. For example, the constricted region 606 may have a variable constricted width 712; the channel walls surrounding the constricted region 606 may be curved or jagged.

In some embodiments, the constricted region 608 is bounded by straight, parallel channel walls.

In some embodiments, the microfluidic device 800 is made of a thermoplastic polymer, for example, by using the process 300. In additional embodiments, the microfluidic device 800 is configured to withstand high fluid pressure without deformation of the constricted regions.

Figure 9:
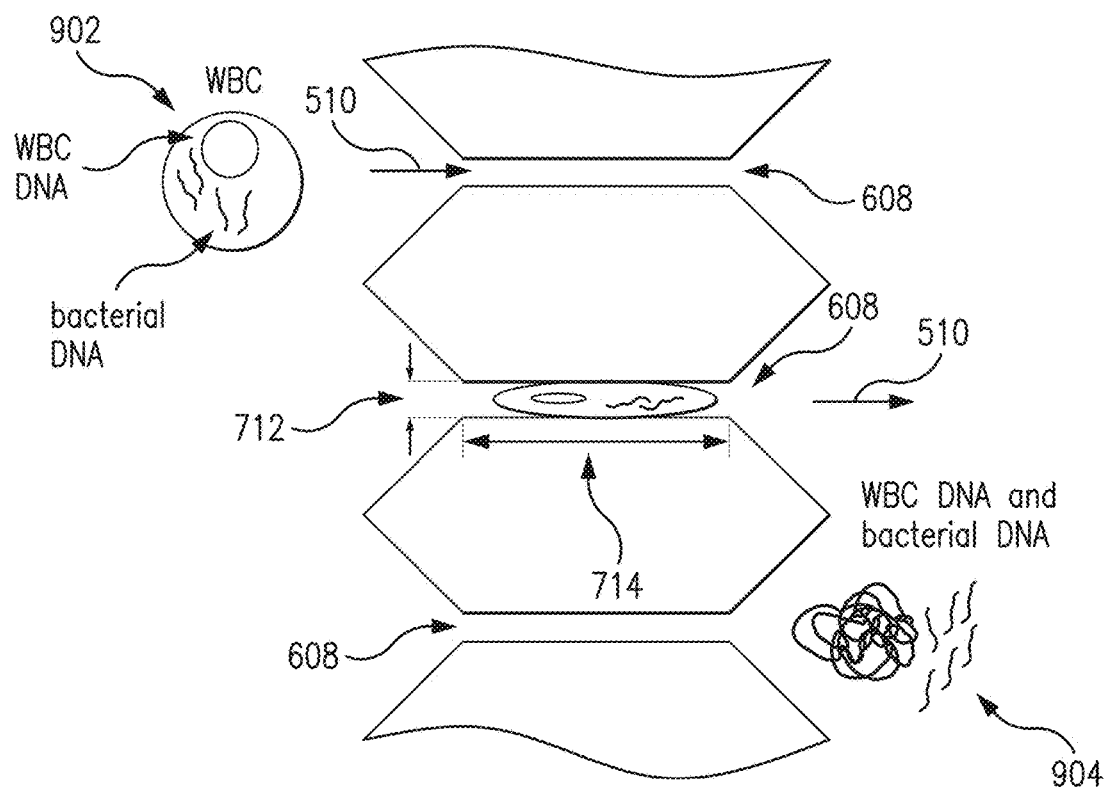
FIG. 9 shows a schematic illustration of the lysis mechanism in accordance with an embodiment of the invention.

FIG. 9 shows a schematic illustration of cell lysis in accordance with an embodiment of the invention. As illustrated in FIG. 9, when cells 902 pass through the constricted regions 608 of the microfluidic channels 502, they are simultaneously compressed and accelerated, causing increased (mechanical) shear stress and subsequent disruption of the cellular membrane. The disruption of the cellular membrane results in cell DNA 904 being suspended in the fluid. Where, for example, infected white blood cells are flowing through the device 800, the sheared cell DNA 904 may include both white-blood-cell DNA and bacterial DNA.

In one non-limiting embodiment, one way of characterizing the extent of cellular damage, hence cell lysis, is to determine the energy dissipation rate (EDR). The EDR describes the rate of work on the cell. It is an intrinsic property that includes both extensional and shear flows. The EDR is largest (indicating greater cellular damage) at the entrance of a constriction where the extensional and shear flows are greatest. The EDR decreases substantially one orifice diameter upstream of the constriction. Thus, a single, long constriction (which, in addition, can suffer from higher back pressure) is less effective at causing cellular damage than a series of constrictions and expansions. In general, it is preferable to design the microfluidic device 800 so that it achieves a high EDR without suffering from high backpressure and clogging from the released nuclear material. In addition, in some embodiments, not all of the cells may be lysed at a single constricted region 608 (sometimes also referred to as a nozzle), but rather may be progressively lysed along the length of the channel as they flow through multiple constricted regions 608 (sometimes also referred to as multiple nozzles).

Figure 10A:
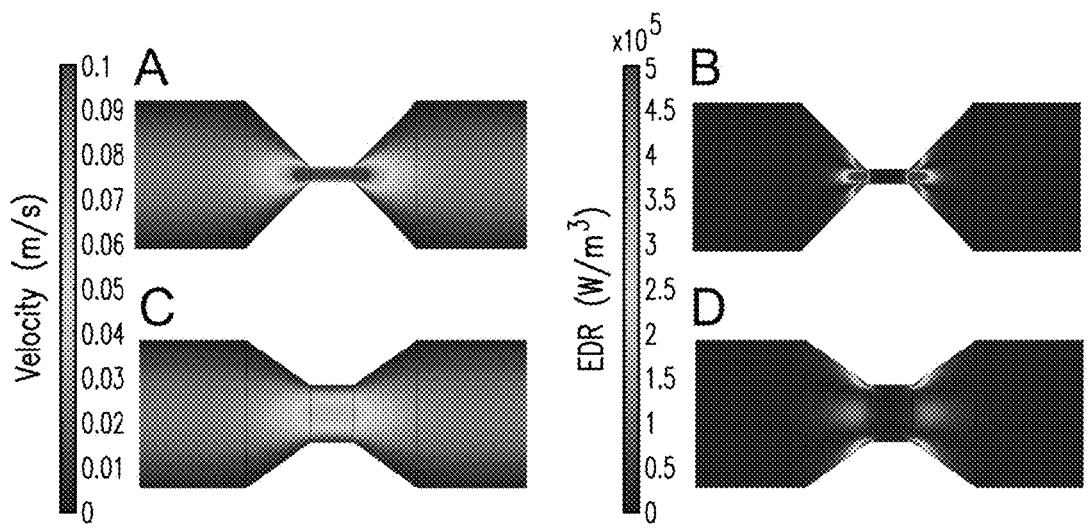
FIGS. 10A and 10B show graphs of simulated EDR values for a 5 µm constriction and a 20 µm constriction.
Figure 10B:
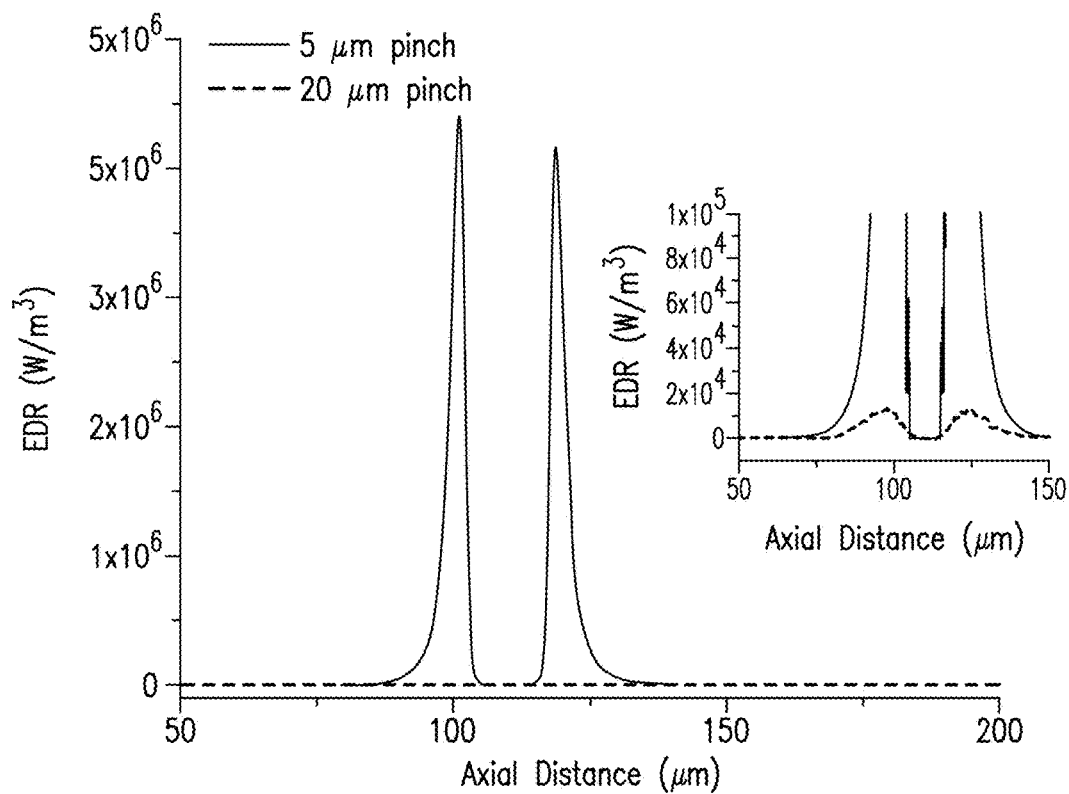

FIGS. 10A and 10B show graphs of simulated EDR values for a 5 μm constriction and a 20 μm constriction. More particularly, FIG. 10A shows the velocity (A) and EDR (B) for a 5 μm constriction, and the velocity (C) and EDR (D) for a 20 μm constriction. The greatest EDR is at the entrance and exit to the constriction. For the 5 μm constriction, the calculated EDR is two orders of magnitude greater than for the 20 μm constriction. This is better illustrated in FIG. 10B, where the EDR along the center line of the channel is plotted. The 5 μm constriction results in a maximum EDR of $4.5 \times 10^6$ W/m$^3$. The 20 μm constriction results in a maximum EDR of $2 \times 10^4$ W/m$^3$.

In some embodiments of the invention, the microfluidic device 800 is used in a process for continuous flow cell lysis. In some embodiments, the process may begin by causing fluid to flow through the microfluidic device 800, whereby cells in the fluid are lysed, wherein the microfluidic device 800 comprises one or more microfluidic channels 502, each channel 502 comprising constricted regions 608 and non-constricted regions 606 separating the constricted regions 608, wherein the constricted regions are configured to disrupt the cellular membranes of cells 902 in fluid flowing through the one or more microfluidic channels 502. In some embodiments, before causing the fluid to flow through the microfluidic device 800, the microfluidic device 800 is primed to eliminate biofouling. As a non-limiting example, 2 g/l pluronic F68 (Sigma Aldrich) may be used for priming. In some embodiments, causing fluid to flow through the microfluidic device 800 may comprise pumping fluid (for example, by using a syringe) or using negative pressure.

In some embodiments, cells 902 are lysed at a flow rate sufficient to cause increased (mechanical) shear stress on the cells passing through the constricted regions as described herein. In some embodiments, the flow rate is from about 20 μL/min to about 2000 μL/min. In other embodiments, the flow rate is from about 20 μL/min to about 1000 μL/min. In still other embodiments, the flow rate may be from about 50 to about 500 μL/min. In further embodiments, the flow rate may be from about 50 to about 200 μL/min. In additional embodiments, the flow rate is about 100 μL/min. The flow rate enables the processing of hundreds to thousands of cells 902 in minutes.

Figure 11:
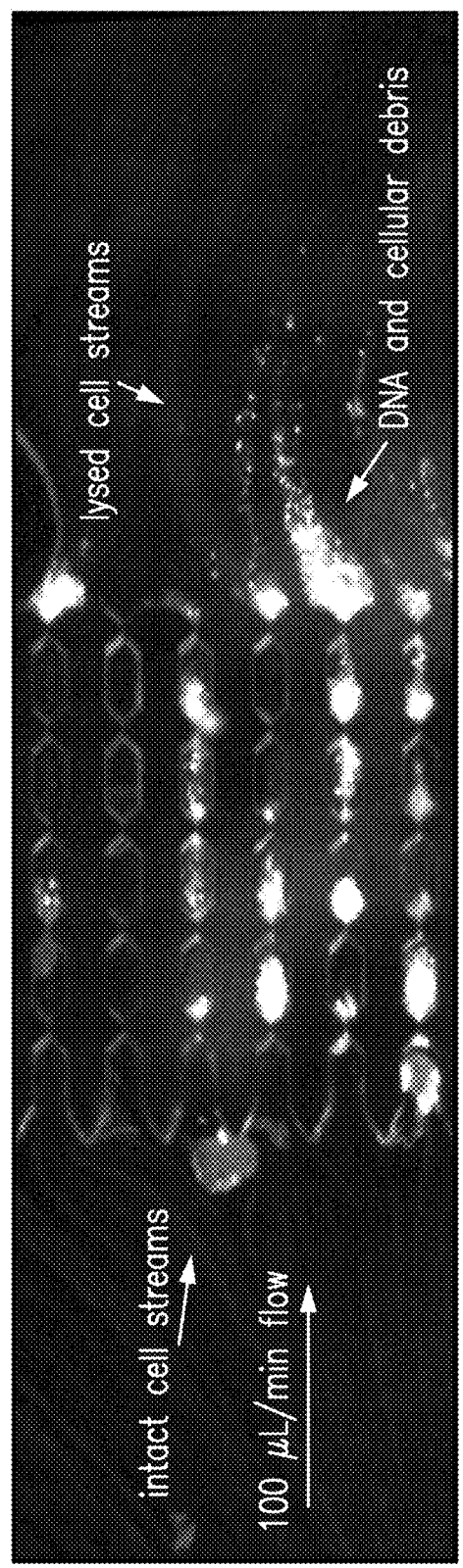
FIG. 11 shows a photograph of cells being lysed in a microfluidic device in accordance with an embodiment of the invention.

FIG. 11 shows a photograph of cells 902 being lysed in a microfluidic device 800 in accordance with an embodiment of the invention. As illustrated in FIG. 11, as intact white blood cells (WBC) 902 (shown as containing white blood cell DNA in a nucleus and bacterial DNA in the cell) flow through the microfluidic channels 502 they are lysed, leaving DNA 904 (white blood cell DNA and bacterial DNA) and cellular debris suspended in the fluid stream.

Some embodiments may be used in micro total analysis systems for many applications, including cancer diagnostic tools based on extracted circulating tumor cells.

EXAMPLES

The present invention is described by reference to the following Examples, which are offered by way of illustration and are not intended to limit the invention in any manner. Standard techniques well known in the art or the techniques specifically described below were utilized.

Example 1

The method for continuous flow cell lysis in a microfluidic device 800, according to some embodiments of the invention, was tested under four scenarios.

According to a first embodiment, the method was performed using a microfluidic device 800 comprising 18 microfluidic channels 502 each having 1 constricted region with a 3 μm constricted width ("single nozzle").

According to a second embodiment, the method was performed by adding a detergent to the single-nozzle configuration above ("single nozzle+detergent"). The detergent comprised the addition of 0.1% Triton X-100 to the fluid flowing through the microfluidic device 800.

According to a third embodiment, the method was performed using a microfluidic device 800 comprising 20 microfluidic channels 502 each having 4 constricted regions with a 3 μm constricted width ("multi-nozzle (3 μm)").

According to a fourth embodiment, the method was performed using a microfluidic device 800 comprising 20 microfluidic channels 502 each having 4 constricted regions with a 5 μm constricted width ("multi-nozzle (5 μm)").

Each of the above four embodiments comprised an OSTE polymer made from an OSTEmer Allyl 30 prepolymer as the thermoplastic polymer. The fluid that was caused to be flowed through the microfluidic devices 800 comprised a 5 mL sample of red blood cells resuspended into 20 mL of a phosphate buffer saline, and pumped through the microfluidic devices 800 at a fluid flow rate of 100 μL/min. The percentage of cells lysed was calculated by counting the cells collected in the outlet and comparing that to the number of cells input into the lysis device.

Figure 12:
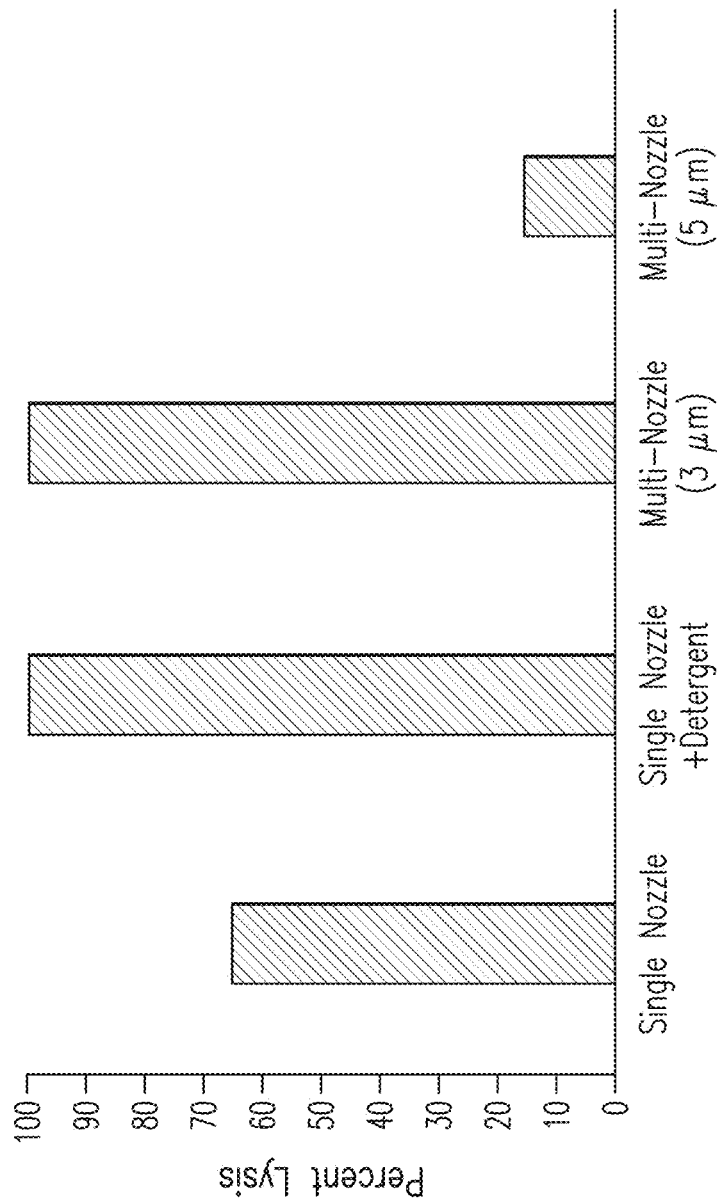
FIG. 12 shows a bar graph comparing results of percent cell lysis with different microfluidic devices.

As shown in FIG. 12, 65% of the cells were lysed in the single-nozzle scenario; nearly 100% were lysed in the single-nozzle+detergent scenario; nearly 100% were lysed in the multi-nozzle (3 μm) scenario; and 15% were lysed in the multi-nozzle (5 μm) scenario.

According to these embodiments, the cellular debris resulting from the lysed cells did not cause substantial clogging of the nozzles, and any DNA remaining after lysis could be removed by flushing at an increased flow rate.

Example 2

The method for continuous flow cell lysis in a microfluidic device 800, according to some embodiments of the invention, was tested under two scenarios.

According to a first embodiment, the method was performed using a microfluidic device 800 comprising 40 microfluidic channels 502 each having 10 constricted regions 608, where the constricted width of the first five constricted regions 608 along the fluid flow path 510 was 6.5 μm and the constricted width of the last five constricted regions 608 along the fluid flow path 510 was 5 μm; the constricted length was 15 μm; the non-constricted width was 52 μm and the non-constricted length was 80 μm. The thermoplastic polymer was an OSTE polymer made from an OSTEmer Allyl 30 prepolymer ("OSTE").

According to a second embodiment, the first embodiment was modified in that the thermoplastic polymer was PDMS ("PDMS").

The fluid caused to be flowed through the microfluidic devices 800 comprised MDA-MB-231 human breast cancer cells diluted to 105 cells/mL in media, pumped at a fluid flow rate of 100 μL/min for 2 minutes. Viable cell density was counted using a hemocytometer.

Figure 13:
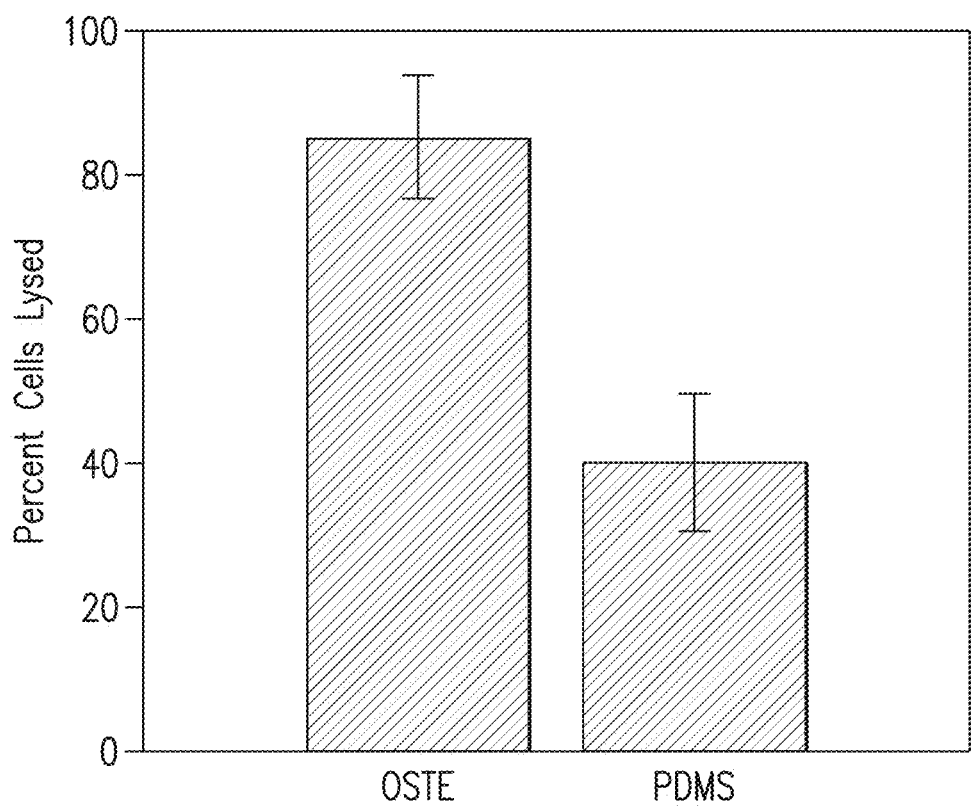
FIG. 13 shows a bar graph comparing results of lysing cells with a microfluidic device made of PDMS- and OSTE-based polymers.

As shown in FIG. 13, 85%±8% of the cells were lysed in the OSTE scenario; 40%±9% of cells were lysed in the PDMS scenario.

According to these embodiments, the cellular debris resulting from the lysed cells did not cause substantial clogging of the channels.

While various embodiments of the present invention have been described above, it should be understood that they have been presented by way of example only, and not limitation. Thus, the breadth and scope of the present invention should not be limited by any of the above-described exemplary embodiments. Variations of the embodiments described above may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A method for fabricating a microfluidic device using soft-lithography replica molding, comprising:
    fabricating a first piece of the microfluidic device in a mold, the first piece including at least one microchannel having features sized to provide for mechanical cell lysis, the features including constricted regions and non-constricted regions separating the constricted regions, the non-constricted regions being shaped to converge at the ends into the constricted regions, wherein fabricating the first piece comprises:
        pouring a first layer of a thermoplastic prepolymer onto the mold; and
        partially curing the first layer under exposure to UV-light;
    fabricating a second piece of the microfluidic device on a glass slide, wherein fabricating the second piece comprises:
        coating the glass slide with a layer of the thermoplastic prepolymer; and
        partially curing the layer coated on the glass slide under exposure to UV-light;
    removing the partially cured first piece from the mold, wherein the partially cured first layer is removed from the mold without loss of the features of the at least one microchannel;
    contacting the first piece to the second piece; and
    bonding the first piece and the second piece together on the glass slide by curing the contacted first and second pieces under exposure to UV-light.

2. The method of claim 1, wherein the microfluidic device includes one or more channels comprising features including constricted regions and non-constricted regions separating the constricted regions, wherein the constricted regions are configured to mechanically lyse cells.

3. The method of claim 2, wherein the one or more microfluidic channels are parallel to each other.

4. The method of claim 2, wherein the non-constricted regions are arranged in a honeycomb-like pattern.

5. The method of claim 2, wherein each of the non-constricted regions has a width of 40-100 μm, and each of the constricted regions has a width of 3-10 μm.

6. The method of claim 2, wherein each of the non-constricted regions has a length of 60-120 μm, and each of the constricted regions has a length of 10-20 μm.

7. The method of claim 2, wherein there are 1-40 microfluidic channels.

8. The method of claim 2, wherein each microfluidic channel comprises 3-15 constricted regions.

9. The method of claim 2, wherein each microfluidic channel comprises a first segment of constricted regions along a fluid flow path having a width of 6-8 μm and a second segment of constricted regions along a fluid flow path having a width of 4-6 μm.

10. The method of claim 2, wherein each of the constricted regions has a width of 2.5-4.5 μm.

11. The method of claim 2, wherein each of the microfluidic channels has 4 constricted regions and each constricted region has a width of 3 μm.

12. The method of claim 2, wherein there are 20 microfluidic channels.

13. The method of claim 2, wherein there are 40 microfluidic channels.

14. The method of claim 2, wherein the microfluidic channels are configured to support a flow rate of from about 20 μ/min to about 2000 μL/min.

15. The method of claim 2, wherein the microfluidic device is configured to support a cell-lysis rate of 85-100%.

16. The method of claim 1, wherein the thermoplastic prepolymer comprises an off-stoichiometry thiol-ene (OSTE) prepolymer.

17. The method of claim 16, wherein the OSTE prepolymer has an excess of allyl groups.

18. The method of claim 1, wherein bonding the first piece and the second piece together on the glass slide further comprises baking the first and second pieces.

19. The method of claim 1, wherein fabricating the first piece further comprises:
   pouring a second layer of the thermoplastic prepolymer onto the mold; and
   degassing the second layer under vacuum.

20. The method of claim 1, wherein fabricating the first piece further comprises removing any air bubbles from the first piece.

21. The method of claim 1, wherein bonding the first piece and the second piece together on the glass slide further comprises baking the first and second pieces at a temperature close to the glass transition temperature of a thermoplastic polymer made from the thermoplastic prepolymer.

22. The method of claim 1, wherein fabricating the first piece of the microfluidic device further comprises applying a release agent onto the mold.

23. The method of claim 1, wherein fabricating the first piece of the microfluidic device further comprises degassing the first layer under vacuum.

24. The method of claim 1, wherein fabricating the second piece of the microfluidic device further comprises applying a release agent onto the glass.

\* \* \* \* \*

UNITED STATES PATENT AND TRADEMARK OFFICE
CERTIFICATE OF CORRECTION

PATENT NO. : 10,137,673 B2  
APPLICATION NO. : 14/586576  
DATED : November 27, 2018  
INVENTOR(S) : Ian M. White et al.

It is certified that error appears in the above-identified patent and that said Letters Patent is hereby corrected as shown below:

On the Title Page

Replace:
(73) Assignee: Canon U.S. Life Sciences, Inc.,
           Rockville, MD (US)

With:
(73) Assignee: University of Maryland, College Park,
           College Park, MD (US)

Signed and Sealed this
Twenty-second Day of October, 2019

Andrei Iancu
*Director of the United States Patent and Trademark Office*